(12) United States Patent
Ramasamy

(10) Patent No.: US 11,246,916 B2
(45) Date of Patent: Feb. 15, 2022

(54) COMPOSITIONS AND METHODS FOR DETOXIFYING BACTERIAL ENDOTOXINS

(71) Applicant: RHOGEN BIOTECH LLC, Mansfield, MA (US)

(72) Inventor: Sundaram Ramasamy, Mansfield, MA (US)

(73) Assignee: RHOGEN BIOTECH LLC, Mansfield, MA (US)

(*) Notice: Subject to any disclaimer, the term of this patent is extended or adjusted under 35 U.S.C. 154(b) by 0 days.

(21) Appl. No.: 17/082,961

(22) Filed: Oct. 28, 2020

(65) Prior Publication Data

US 2021/0145939 A1    May 20, 2021

Related U.S. Application Data

(63) Continuation of application No. PCT/US2020/035533, filed on Jun. 1, 2020.

(60) Provisional application No. 62/855,907, filed on May 31, 2019.

(51) Int. Cl.

| | |
|---|---|
| *A61K 38/45* | (2006.01) |
| *A23L 33/105* | (2016.01) |
| *A23L 33/135* | (2016.01) |
| *A61P 31/04* | (2006.01) |
| *C12N 9/10* | (2006.01) |
| *A61K 35/00* | (2006.01) |
| *A23L 33/00* | (2016.01) |
| *A23C 9/12* | (2006.01) |
| *A61K 35/741* | (2015.01) |

(52) U.S. Cl.
CPC ............ *A61K 38/45* (2013.01); *A23C 9/1203* (2013.01); *A23L 33/105* (2016.08); *A23L 33/135* (2016.08); *A23L 33/40* (2016.08); *A61K 35/741* (2013.01); *A61P 31/04* (2018.01); *C12N 9/13* (2013.01); *C12Y 208/01001* (2013.01); *A23V 2002/00* (2013.01); *A61K 2035/115* (2013.01)

(58) Field of Classification Search
CPC .................. A61K 38/45; A61K 35/741; A61K 2035/115; C12N 9/13; C12Y 208/01001
See application file for complete search history.

(56) References Cited

U.S. PATENT DOCUMENTS

| | | |
|---|---|---|
| 5,770,423 A | 6/1998 | Beach et al. |
| 6,290,952 B1 | 9/2001 | Poelstra et al. |
| 8,557,545 B2 | 10/2013 | Velders et al. |
| 2006/0121498 A1 | 6/2006 | Murphy et al. |
| 2010/0261213 A1 | 10/2010 | Ryu et al. |
| 2012/0093868 A1 | 4/2012 | Masignani et al. |
| 2013/0295164 A1 | 11/2013 | Haensler et al. |
| 2015/0037419 A1 | 2/2015 | Bazile et al. |
| 2015/0240226 A1 | 8/2015 | Mathur et al. |

FOREIGN PATENT DOCUMENTS

| | | |
|---|---|---|
| EP | 3097188 B1 | 8/2018 |
| WO | 00/37943 A1 | 6/2000 |
| WO | 2012104589 A1 | 8/2012 |
| WO | 2019183208 A1 | 9/2019 |

OTHER PUBLICATIONS

Parca et al. "Phosphate binding sites identification in protein structures", Nucleic Acids Research, 2011, vol. 39, No. 4 1231-1242, Published online Oct. 24, 2010 (Year: 2010).*
Search Report, dated May 27, 2021, Uniport (Year: 2021).*
International Search Report and Written Opinion from corresponding International Application No. PCT/US2020/035533 dated Sep. 21, 2020.

* cited by examiner

*Primary Examiner* — Ruth A Davis

(74) *Attorney, Agent, or Firm* — Johnson, Marcou, Isaacs & Nix, LLC; F. Brent Nix, Esq.; Rachel D. Rutledge, Esq.

(57) ABSTRACT

Compositions comprising a rhodanese with a phosphate-binding motif and methods of detoxifying bacterial endotoxins with such compositions.

23 Claims, 2 Drawing Sheets
Specification includes a Sequence Listing.

```
        10         20         30         40         50
MVHQVLYRAL VSTKWLAESI RTGKLGPGLR VLDASWYSPG TREARKEYLE
        60         70         80         90        100
RHVPGASFFD IEECRDTASP YEMMLPSEAG FAEYVGRLGI SNHTHVVVYD
       110        120        130        140        150
GEHLGSFYAP RVWWMFRVFG HRTVSVLNGG FRNWLKEGHP VTSEPSRPEP
       160        170        180        190        200
AVFKATLDRS LLKTYEQVLE NLESKRFQLV DSRSQGRFLG TEPEPDAVGL
       210        220        230        240        250
DSGHIRGAVN MPFMDFLTED GFEKGPEELR ALFQTKKVDL SQPLIATCEYS  (SDM Active
sites)
       260        270        280        290
GVRACHVALA AYLCGKPDVA VYDGSWSEWF RRAPPESRVS QGKSEKA
```

FIG. 2

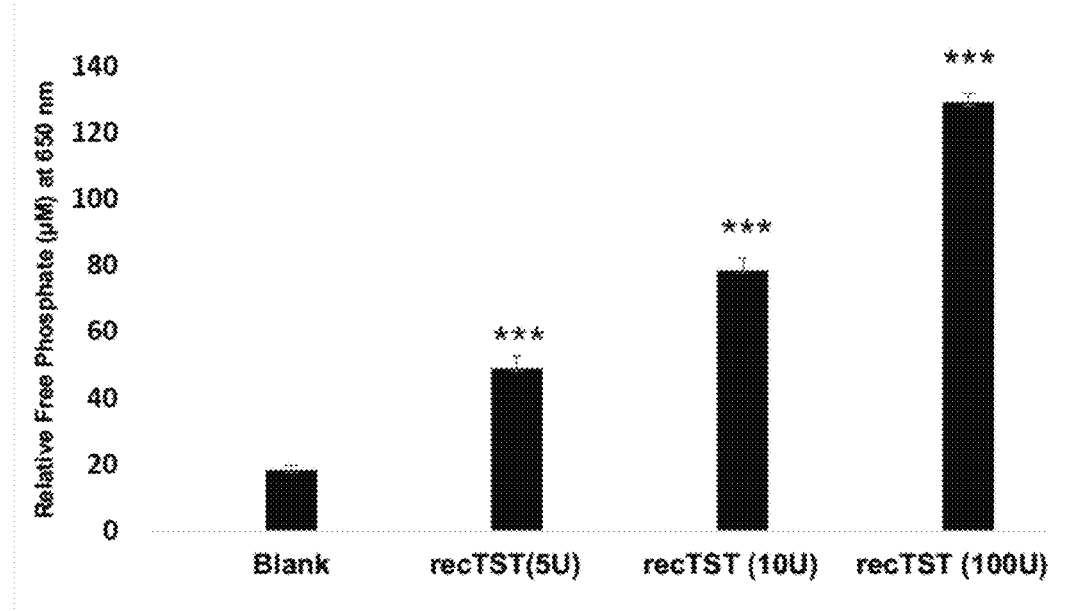

FIG. 3

SEQUENCE LISTING

<160> NUMBER OF SEQ ID NOS: 16

<210> SEQ ID NO 1
<211> LENGTH: 297
<212> TYPE: PRT
<213> ORGANISM: Homo sapiens

<400> SEQUENCE: 1

Met Val His Gln Val Leu Tyr Arg Ala Leu Val Ser Thr Lys Trp Leu
1               5                   10                  15

Ala Glu Ser Ile Arg Thr Gly Lys Leu Gly Pro Gly Leu Arg Val Leu
            20                  25                  30

Asp Ala Ser Trp Tyr Ser Pro Gly Thr Arg Glu Ala Arg Lys Glu Tyr
        35                  40                  45

Leu Glu Arg His Val Pro Gly Ala Ser Phe Phe Asp Ile Glu Glu Cys
    50                  55                  60

Arg Asp Thr Ala Ser Pro Tyr Glu Met Met Leu Pro Ser Glu Ala Gly
65                  70                  75                  80

Phe Ala Glu Tyr Val Gly Arg Leu Gly Ile Ser Asn His Thr His Val
                85                  90                  95

Val Val Tyr Asp Gly Glu His Leu Gly Ser Phe Tyr Ala Pro Arg Val
            100                 105                 110

Trp Trp Met Phe Arg Val Phe Gly His Arg Thr Val Ser Val Leu Asn
        115                 120                 125

Gly Gly Phe Arg Asn Trp Leu Lys Glu Gly His Pro Val Thr Ser Glu
130                 135                 140

Pro Ser Arg Pro Glu Pro Ala Val Phe Lys Ala Thr Leu Asp Arg Ser
145                 150                 155                 160

Leu Leu Lys Thr Tyr Glu Gln Val Leu Glu Asn Leu Glu Ser Lys Arg
                165                 170                 175

Phe Gln Leu Val Asp Ser Arg Ser Gln Gly Arg Phe Leu Gly Thr Glu
            180                 185                 190

Pro Glu Pro Asp Ala Val Gly Leu Asp Ser Gly His Ile Arg Gly Ala
        195                 200                 205

Val Asn Met Pro Phe Met Asp Phe Leu Thr Glu Asp Gly Phe Glu Lys
    210                 215                 220

Gly Pro Glu Glu Leu Arg Ala Leu Phe Gln Thr Lys Lys Val Asp Leu
225                 230                 235                 240

Ser Gln Pro Leu Ile Ala Thr Cys Arg Lys Gly Val Thr Ala Cys His
                245                 250                 255

Val Ala Leu Ala Ala Tyr Leu Cys Gly Lys Pro Asp Val Ala Val Tyr
            260                 265                 270

Asp Gly Ser Trp Ser Glu Trp Phe Arg Arg Ala Pro Pro Glu Ser Arg
        275                 280                 285

Val Ser Gln Gly Lys Ser Glu Lys Ala
    290                 295

<210> SEQ ID NO 2
<211> LENGTH: 6
<212> TYPE: PRT
<213> ORGANISM: Homo sapiens

<400> SEQUENCE: 2

Cys Arg Lys Gly Val Thr
1               5

-continued

```
<210> SEQ ID NO 3
<211> LENGTH: 7
<212> TYPE: PRT
<213> ORGANISM: Artificial Sequence
<220> FEATURE:
<223> OTHER INFORMATION: Synthetic

<400> SEQUENCE: 3

Cys Glu Tyr Ser Gly Val Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic

<400> SEQUENCE: 4

Cys Glu Phe Ser Gly Val Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Cys Arg Glu Gly Ser Val Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic

<400> SEQUENCE: 6

Cys Arg Tyr Ser Gly Val Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic

<400> SEQUENCE: 7

Cys Glu Thr Ser Gly Val Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic

<400> SEQUENCE: 8

Cys Glu Tyr Ser Gly Val Arg
1               5

<210> SEQ ID NO 9
```

```
<211> LENGTH: 7
<212> TYPE: PRT
<213> ORGANISM: Artificial Sequence
<220> FEATURE:
<223> OTHER INFORMATION: Synthetic

<400> SEQUENCE: 9

Cys Glu Tyr Ser Gly Glu Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic

<400> SEQUENCE: 10

Cys Arg Lys Ser Ser Glu Arg
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic

<400> SEQUENCE: 11

Cys Glu Lys Ser Ser Glu Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic

<400> SEQUENCE: 12

Cys Glu Lys Gly Ser Glu Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic

<400> SEQUENCE: 13

Cys Arg Gly Ser Ser Glu Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic

<400> SEQUENCE: 14

Cys Glu Phe Ser Ser Glu Arg
1               5

<210> SEQ ID NO 15
<211> LENGTH: 7
```

```
<212> TYPE: PRT
<213> ORGANISM: Artificial Sequence
<220> FEATURE:
<223> OTHER INFORMATION: Synthetic

<400> SEQUENCE: 15

Cys Glu Tyr Ser Ser Glu Arg
1               5

<210> SEQ ID NO 16
<211> LENGTH: 298
<212> TYPE: PRT
<213> ORGANISM: Homo sapiens

<400> SEQUENCE: 16

Met Val His Gln Val Leu Tyr Arg Ala Leu Val Ser Thr Lys Trp Leu
1               5                   10                  15

Ala Glu Ser Ile Arg Thr Gly Lys Leu Gly Pro Gly Leu Arg Val Leu
            20                  25                  30

Asp Ala Ser Trp Tyr Ser Pro Gly Thr Arg Glu Ala Arg Lys Glu Tyr
        35                  40                  45

Leu Glu Arg His Val Pro Gly Ala Ser Phe Phe Asp Ile Glu Glu Cys
    50                  55                  60

Arg Asp Thr Ala Ser Pro Tyr Glu Met Met Leu Pro Ser Glu Ala Gly
65                  70                  75                  80

Phe Ala Glu Tyr Val Gly Arg Leu Gly Ile Ser Asn His Thr His Val
                85                  90                  95

Val Val Tyr Asp Gly Glu His Leu Gly Ser Phe Tyr Ala Pro Arg Val
            100                 105                 110

Trp Trp Met Phe Arg Val Phe Gly His Arg Thr Val Ser Val Leu Asn
        115                 120                 125

Gly Gly Phe Arg Asn Trp Leu Lys Glu Gly His Pro Val Thr Ser Glu
    130                 135                 140

Pro Ser Arg Pro Glu Pro Ala Val Phe Lys Ala Thr Leu Asp Arg Ser
145                 150                 155                 160

Leu Leu Lys Thr Tyr Glu Gln Val Leu Glu Asn Leu Glu Ser Lys Arg
                165                 170                 175

Phe Gln Leu Val Asp Ser Arg Ser Gln Gly Arg Phe Leu Gly Thr Glu
            180                 185                 190

Pro Glu Pro Asp Ala Val Gly Leu Asp Ser Gly His Ile Arg Gly Ala
        195                 200                 205

Val Asn Met Pro Phe Met Asp Phe Leu Thr Glu Asp Gly Phe Glu Lys
    210                 215                 220

Gly Pro Glu Glu Leu Arg Ala Leu Phe Gln Thr Lys Lys Val Asp Leu
225                 230                 235                 240

Ser Gln Pro Leu Ile Ala Thr Cys Glu Tyr Ser Gly Val Arg Ala Cys
                245                 250                 255

His Val Ala Leu Ala Ala Tyr Leu Cys Gly Lys Pro Asp Val Ala Val
            260                 265                 270

Tyr Asp Gly Ser Trp Ser Glu Trp Phe Arg Arg Ala Pro Pro Glu Ser
        275                 280                 285

Arg Val Ser Gln Gly Lys Ser Glu Lys Ala
    290                 295
```

COMPOSITIONS AND METHODS FOR DETOXIFYING BACTERIAL ENDOTOXINS

CROSS-REFERENCE TO RELATED APPLICATIONS

This application is a continuation of International Application No. PCT/US2020/035533, filed Jun. 1, 2020, which claims the benefit of U.S. Provisional Application No. 62/855,907, filed May 31, 2019. The entire contents of the above-identified applications are hereby fully incorporated herein by reference.

REFERENCE TO AN ELECTRONIC SEQUENCE LISTING

The contents of the electronic sequence listing ("RHOG-0100US-TRACK1_ST25.txt"; Size is 7,825 bytes and it was created on Oct. 28, 2020) is herein incorporated by reference in its entirety.

TECHNICAL FIELD

The subject matter disclosed herein is generally directed to compositions and methods for detoxifying bacterial endotoxins.

BACKGROUND

Toxicity from bacterial endotoxins (e.g., lipopolysaccharide) is an important contributing factor to a variety of health problems. There is a need for novel reagents capable of detoxifying bacterial endotoxins in vitro and in vivo.

SUMMARY

In one aspect, the present disclosure provides a composition comprising an engineered or non-naturally occurring rhodanese comprising a phosphate-binding motif.

In some embodiments, the rhodanese has a dephosphorylation activity. In some embodiments, the rhodanese is capable of dephosphorylating a bacterial endotoxin. In some embodiments, the bacterial endotoxin is lipopolysaccharide (LPS) or lipoteichoic acid (LTA). In some embodiments, the phosphate-binding motif comprises a sequence of $CX_1X_2X_3X_4X_5R$, wherein $X_1$ comprises 1 amino acid, $X_2$ comprises 1 amino acid, $X_3$ comprises 1 amino acid, $X_4$ comprises 1 amino acid, and $X_5$ comprises 1 amino acid. In some embodiments, $X_1$ is E or R; $X_2$ is Y, F, E, T, K, or G; $X_3$ is S or G; $X_4$ is S or G; and $X_5$ is V or E.

In some embodiments, the phosphate-binding motif comprises a sequence of SEQ ID NOs. 3-15. In some embodiments, the phosphate-binding motif comprises a sequence of SEQ ID NO. 3. In some embodiments, the rhodanese comprises a sequence of SEQ ID NO. 16. In some embodiments, the rhodanese is or is derived from a mammalian intestine rhodanese, human rhodanese, or bovine liver rhodanese.

In some embodiments, the composition comprises one or a population of microorganisms producing the rhodanese. In some embodiments, the microorganisms are probiotic bacteria. In some embodiments, the composition is a food product, a nutritional formulation, a diary product, or a combination thereof. In some embodiments, the food product comprises a plant of a part thereof. In some embodiments, the diary product is non-pasteurized diary, partially pasteurized milk, a milk component, or a milk fat globule membrane component.

In another aspect, the present disclosure provides a pharmaceutical formulation comprising the composition herein. In some embodiments, the pharmaceutical formulation further comprises a stabilizer, activator, carrier, osmotic agent, propellant, disinfectant, protective agent, diluent, nutritional agent, excipient, or a combination thereof. In some embodiments, the pharmaceutical formulation is a vaccine.

In one aspect, the present disclosure provides a method for treating a health condition induced by a bacterial endotoxin, the method comprising administering a composition comprising an effective amount of rhodanese to a subject in need thereof, wherein the rhodanese is capable of detoxifying the bacterial endotoxin. In some embodiments, the composition is the engineered, non-naturally occurring rhodanese herein, or the pharmaceutical formulation comprises the engineered, non-naturally occurring rhodanese herein. In some embodiments, the composition comprises a pharmaceutical formulation. In some embodiments, the administration is performed orally, topically, or intravenously.

In some embodiments, the health condition is a LPS-mediated, LPS-induced, or LPS-exacerbated disease. In some embodiments, the health condition is bowel diseases, *Clostridium difficile* infection, modulation of gut microbiota, alternation of bacterial over growth, Small intestinal bacterial overgrowth, antibiotic-associated diarrhea (AAD), gastrointestinal tract infections, abdominal infections, sepsis, septic shock, systemic inflammatory response syndrome, meningococcemia, trauma, hemorrhagic shock, burns, surgery, organ transplantation, liver diseases, pancreatitis, enterocolitis, periodontal diseases, pneumonia, cystic fibrosis, asthma, coronary heart diseases, congestive heart failure, kidney diseases hypophosphatasia, hemolytic uremic syndrome, renal dialysis, preserving renal function, autoimmune diseases, cancers, Alzheimer's disease, rheumatoid arthritis, lupus, systemic lupus erythematosus, metabolic disorders, obesity, diabetes, dyslipidemia, insulin resistant syndromes, metabolic syndrome, steatohepatitis, fatty liver, non-alcoholic fatty liver diseases, hyperglycemia, glucose intolerance, impaired glucose tolerance, insulin resistance, hyperlipidemia, hypertriglyceridemia, hypercholesterolemia, low HDL levels, high LDL levels, abdominal obesity, atherosclerosis, hypertension, and cardiovascular diseases, or a combination thereof. In some embodiments, the health condition is an infection by one or more bacteria producing the endotoxin. In some embodiments, the composition is effective to increase the number of commensal bacteria in the gastrointestinal tract, decrease the number of pathogenic bacteria in the gastrointestinal tract, or increase the number of commensal bacteria and decrease the number of pathogenic bacteria in the gastrointestinal tract, thereby modulating gastrointestinal tract flora levels in the subject.

In one aspect, the present disclosure provides a method of making a pharmaceutical formulation comprising a non-toxic bacterial endotoxin, the method comprising detoxifying a toxic endotoxin with the composition herein, or the pharmaceutical formulation herein, thereby producing the non-toxic bacterial endotoxin.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 2 shows site-directed mutagenesis of recombinant human rhodanese enzyme and its function in dephosphorylation of the *E. coli*'s LPS. Engineered rhodanese sequence (SEQ ID NO. 16) is shown with engineered sequence underlined (SEQ ID NO. 3).

FIG. 3 Detoxification of *E. coli* LPS by an exemplary engineered human rhodanese.

Figure 1:
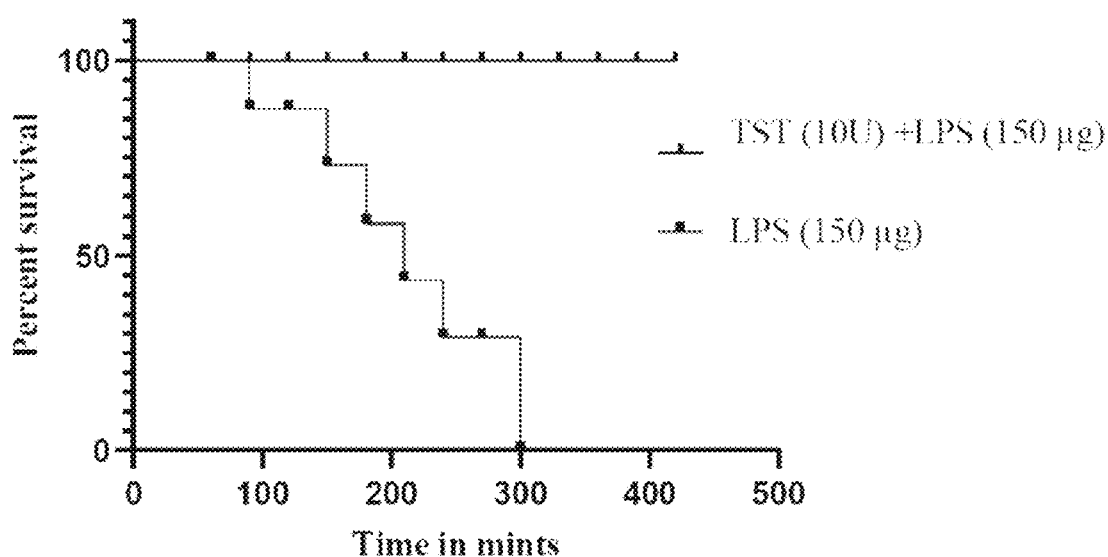
FIG. 1 demonstrates the detoxification of LPS by a rhodanese. LPS preincubated with the rhodanese at 10 units/ml was non-toxic to zebrafish at 150 µg/ml LPS, in contrast to the mock treated LPS control. All animals were administered with LPS at 7 dpf. n=8-10 total animals for each sample group. At least three independent experiments were conducted.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The term "about" in relation to a reference numerical value and its grammatical equivalents as used herein can include the numerical value itself and a range of values plus or minus 10% from that numerical value. For example, the amount "about 10" includes 10 and any amounts from 9 to 11. For example, the term "about" in relation to a reference numerical value can also include a range of values plus or minus 10%, 9%, 8%, 7%, 6%, 5%, 4%, 3%, 2%, or 1% from that value.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humor, vitreous humor, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The term "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

A protein or nucleic acid derived from a species means that the protein or nucleic acid has a sequence identical to an endogenous protein or nucleic acid or a portion thereof in the species. The protein or nucleic acid derived from the species may be directly obtained from an organism of the species (e.g., by isolation), or may be produced, e.g., by recombination production or chemical synthesis.

The terms "protein" and "polypeptide" refer to compounds comprising amino acids joined via peptide bonds and may be used interchangeably. As used herein, where "amino acid sequence" is recited it refers to an amino acid sequence of a protein or peptide molecule. An "amino acid sequence" can be deduced from the nucleic acid sequence encoding the protein. However, terms such as "polypeptide" or "protein" are not meant to limit the amino acid sequence to the deduced amino acid sequence, but can include post-translational modifications of the deduced amino acid sequences, such as amino acid deletions, additions, and modifications such as glycosylations and addition of lipid moieties. Also the use of non-natural amino acids, such as D-amino acids to improve stability or pharmacokinetic behavior falls within the scope of the term "amino acid sequence," unless indicated otherwise.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

The present disclosure provides compositions and methods for detoxifying bacterial endotoxins. In one aspect, the present disclosure provides compositions comprising an engineered or non-naturally occurring rhodanese, or a functional domain thereof. The engineered or non-naturally occurring rhodanese may comprise a phosphate-binding motif. The rhodanese may detoxify one or more bacterial endotoxins (e.g., LPS) by dephosphorylation.

In another aspect, the present disclosure further includes methods of detoxifying bacterial endotoxins and related applications. In some embodiments, the applications include methods for treating a health condition, e.g., a condition caused by bacterial endotoxins, by administering a composition comprising a rhodanese or a variant thereof to a subject in need thereof. In certain embodiments, the applications include methods for detoxifying bacterial endotoxins in vitro, e.g., in a pharmaceutical formulation or a product generated in bacteria.

In some embodiments, the present disclosure provides a protein, polynucleotide, and/or vector for use in a variety of diseases. A protein may be especially useful, because of its organ distribution, for use in treating a disease involving the gastro-intestinal tract, kidney skin, liver, lung, brain, fat tissue, or bone. In some embodiments, the present disclosure provides a protein or a polynucleotide and/or vector according said protein for use in treating kidney disease.

Compositions

In an aspect, the present disclosure provides compositions comprising a rhodanese, a functional fragment thereof, and/or or a variant thereof. The compositions may further comprise other components suitable for various applications of the rhodanese.

Rhodanese

A rhodanese (also known as rhodanase, thiosulfate sulfurtransferase (TST), thiosulfate cyanide trans-sulfurase, and thiosulfate thiotransferase) herein refers to a mitochondrial enzyme that detoxifies cyanide ($CN^-$), e.g., by converting it to thiocyanate ($SCN^-$). The term rhodanese as used herein also encompasses a variant of a wildtype rhodanese, e.g., a rhodanese comprising one or more mutations (e.g., substitution, insertion, deletion and/or addition of one or more amino-acids) compared to a wildtype rhodanese counterpart. In some examples, a variant of rhodanese is an engineered, non-naturally occurring variant of rhodanese. The term rhodanese further encompasses a functional fragment of the rhodanese or a variant thereof. The functional fragment may comprise a polypeptide that includes fewer amino acid residues than the original sequence but still confers the enzymatic activity of the original sequence of reference. In some cases, rhodaneses or variants thereof include rhodaneses comprising one or more polymorphisms. Examples of rhodanese with polymorphisms include those described in Rita Cipollone et al., IUBMB Life. 2007 February; 59 (2):51-9; and Marouane Libiad et al., J Biol Chem. 2015 Sep. 25; 290 (39):23579-88, which are incorporated by reference in their entireties.

The rhodanese or a variant thereof may have an activity other than the sulfurtransferase activity. For example, the rhodanese or an engineered or non-naturally occurring form thereof may have a dephosphorylation activity, e.g., an activity capable of dephosphorylating bacterial endotoxins such as lipopolysaccharide (LPS) or lipoteichoic acid (LTA), as well as removing phosphate group(s) from many types of molecules, including, e.g., nucleotides, CpG DNA, flagellin, proteins, ATP and ADP, and alkaloids.

The dephosphorylation activity of the rhodanese on a bacterial endotoxin may be measured by incubating the rhodanese and the endotoxin, and detecting inorganic phosphorus release, e.g., using malachite green solution by spectrophotometric absorbance readings at 650 nm wavelength), e.g., as described in Chen K T et al., Am J Physiol Gastrointest Liver Physiol. 2010 August; 299 (2):G467-75, which is incorporated by reference herein in its entirety.

Examples of rhodanese sequences include those described in Accession No. BAA13327, P00586, EC 2.8.1.1.1/GenBank BAA13327.1, CAA42060.1, UniProtKB/Swiss-Prot: P25325, and in R. Pallini et al, Biochem Biophys Res Commun, 180 (2): 887-893 (1991 October).

In some examples, the rhodanese comprises a sequence of SEQ ID NO. 1 or a portion thereof.

1 mvhqvlyral vstkwlaesi rtgklgpglr vldaswyspg trearkeyle rhvpgasffd
61 ieecrdtasp yemmlpseag faeyvgrlgi snhthvvvyd gehlgsfyap rvwwmfrvfg
121 hrtvsvlngg frnwlkeghp vtsepsrpep avfkatldrs llktyeqvle nleskrfqlv
181 dsrsqgrflg tepepdavgl dsghirgavn mpfmdflted gfekgpeelr alfqtkkvdl
241 sqpliatcrk gvtachvala aylcgkpdva vydgswsewf rrappesrvs qgkseka (SEQ ID NO. 1)

The compositions may comprise homologs and/or orthologs of a rhodanese. The terms "ortholog" and "homolog" are well known in the art. By means of further guidance, a "homolog" of a protein as used herein is a protein of the same species which performs the same or a similar function as the protein it is a homologue of Homologous proteins may but need not be structurally related, or are only partially structurally related. An "ortholog" of a protein as used herein is a protein of a different species which performs the same or a similar function as the protein it is an ortholoque of Orthologous proteins may but need not be structurally related, or are only partially structurally related. Homologs and orthologs may be identified by homology modelling (see, e.g., Greer, Science vol. 228 (1985) 1055, and Blundell et al. Eur J Biochem vol 172 (1988), 513) or "structural BLAST" (Dey F, Cliff Zhang Q, Petrey D, Honig B. Toward a "structural BLAST": using structural relationships to infer function. Protein Sci. 2013 April; 22 (4):359-66. doi: 10.1002/pro.2225). Homologous proteins may but need not be structurally related, or are only partially structurally related.

In some embodiments, the rhodanese may be a rhodandese from a eukaryote, e.g., a mammal. Examples of mammalian rhodanese include mammalian intestine rhodanese, human rhodanese, or bovine rhodanese (e.g., Accession No. P00586). A bovine rhodanese may be a bovine liver rhodanese. In some examples, a rhodanese may be a human rhodanese or a variant thereof. In certain embodiments, the rhodanese may be a rhodanese from a prokaryote, e.g., bacteria such as *E coli*.

Rhodanese Variants

The rhodanese herein may be a variant (e.g., an engineered or non-naturally occurring form) of a wildtype rhodanese. A rhodanese variant may comprise one or more modifications compared to a wildtype counterpart. A rhodanese variant may have the sulfurtransferase activity as a wildtype rhodanese. In alternative cases, the engineered or non-naturally rhodanese may have a reduced or no sulfurtransferase activity. The rhodanese variant may have an activity other than a sulfurtransferase activity, e.g., a dephosphorylation activity.

In some embodiments, the rhodanese or its variant comprises one or more phosphate-binding motifs. The phosphate-binding motifs may bind to a phosphorus atom. In some cases, the phosphate-binding motifs comprise the active-site loop of a rhodanese. In an example, the active-site loop of a rhodanese comprises amino acids corresponding to amino acids 248-253 of a human rhodanese (Accession No. BAA13327) or the sequence of CRKGVT (SEQ ID NO. 2).

In alternative cases, the phosphate-binding motifs comprise a modified active-site loop of a rhodanese. In some embodiments, the amino acid residues of the active-site loop have wide variability which is related to the distinct biological functions played by the rhodanese and variants thereof. For example, the amino acid residues may be varied (e.g., modified, inserted, or deleted) in the active-site loop to alter the binding affinity and/or specificity of the active-loop with a ligand. For example, the phosphate-binding motifs may have one or more additional amino acid residues (e.g., additional 1, 2, 3 or more amino acid) in the active-site loop. Such a modified active-site loop may have a wider catalytic pocket that can accommodate a phosphorous atom, which has a van der Waals radius slightly larger than a sulfur atom. Alternatively or additionally, the phosphate-binding motifs may have one or more amino acid substitutions in the active-site loop. The amino acid side chains extending from this structural element may define the ridge of the catalytic pocket and can play a role in substrate recognition and catalytic activity of phosphorus.

In some embodiments, the phosphate-binding motifs comprise a sequence of $CX_1X_2X_3X_4X_5R$, wherein $X_1$ comprises 1 amino acid, $X_2$ comprises 1 amino acid, $X_3$ comprises 1 amino acid, $X_4$ comprises 1 amino acid, and $X_5$ comprises 1 amino acid. In some examples, $X_1$ is E or R. In some examples, $X_2$ is Y, F, E, T, K, or G. In some examples, $X_3$ is S or G. In some examples, $X_4$ is S or G. In some examples, $X_5$ is V or E. In some examples, $X_1$ is E or R; $X_2$ is Y, F, E, T, K, or G; $X_3$ is S or G; $X_4$ is S or G; and $X_5$ is V or E.

Examples of the sequences of the phosphate-binding motifs include those listed below:

TABLE 1

| SEQ ID NO. | Sequences |
| --- | --- |
| 3 | CEYSGVR |
| 4 | CEFSGVR |
| 5 | CREGSVR |
| 6 | CRYSGVR |
| 7 | CETSGVR |
| 8 | CEYSGVR |
| 9 | CEYSGER |
| 10 | CRKSSER |
| 11 | CEKSSER |
| 12 | CEKGSER |
| 13 | CRGSSER |
| 14 | CEFSSER |
| 15 | CEYSSER |

In some examples, a rhodanese variant is a human rhodanese with the active-site loop sequence of CRKGVT (SEQ ID NO. 2) replaced with one of SEQ ID NOs. 3-15. In a particular example, a rhodanese variant comprises the sequence of:

```
                                                (SEQ ID NO. 16)
MVHQVLYRAL VSTKWLAESI RTGKLGPGLR

VLDASWYSPG TREARKEYLE RHVPGASFFD

IEECRDTASP YEMMLPSEAG FAEYVGRLGI

SNHTHVVVYD GEHLGSFYAP RVWWMFRVFG

HRTVSVLNGG FRNWLKEGHP VTSEPSRPEP

AVFKATLDRS LLKTYEQVLE NLESKRFQLV

DSRSQGRFLG TEPEPDAVGL DSGHIRGAVN

MPFMDFLTED GFEKGPEELR ALFQTKKVDL

SQPLIATCEYS GVRACHVALA AYLCGKPDVA

VYDGSWSEWF RRAPPESRVS QGKSEKA.
```

Polynucleotides and Vectors

In some embodiments, the compositions comprise one or more polynucleotides encoding a rhodanese, a functional fragment thereof, or a variant thereof. In some embodiments, the compositions may comprise a vector comprising one or more polynucleotides encoding a rhodanese, a functional fragment, or a variant thereof.

A vector may be a viral vector (e.g., adenoviral, lentiviral, or adeno-associated viral vector), where virally-derived DNA or RNA sequences are present in the vector for packaging into a virus. Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

Certain vectors may be capable of directing the expression of genes to which they are operatively-linked. Such vectors are referred to herein as "expression vectors." Common expression vectors of utility in recombinant DNA techniques are often in the form of plasmids. A vector may be a recombinant expression vector that comprises a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. As used herein, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

Pharmaceutical Formulations

Further provided herein include pharmaceutical formulations. The pharmaceutical formulation may comprise a rhodanese, a functional fragment thereof, or a variant thereof. The formulations may comprise a therapeutically-effective amount of the active ingredient(s) (e.g., a rhodanese, a functional fragment thereof, or a variant thereof), and a pharmaceutically acceptable carrier. The pharmaceutical formulations may also further comprise diluents, fillers, salts, buffers, stabilizers, solubilizers, activators, osmotic agents, propellants, disinfectants, protective agents, diluents, nutritional agents, excipients, and other materials well known in the art, or a combination thereof. The pharmaceutical formulation can be administered in the form of salts provided the salts are pharmaceutically acceptable. Salts may be prepared using standard procedures known to those skilled in the art of synthetic organic chemistry.

A "pharmaceutical formulation" refers to a composition that usually contains an excipient, such as a pharmaceutically acceptable carrier that is conventional in the art and that is suitable for administration to cells or to a subject. "Pharmaceutically acceptable" as used throughout this specification is consistent with the art and means compatible with the other ingredients of a pharmaceutical composition and not deleterious to the recipient thereof. In some cases, a pharmaceutical formulation is a vaccine.

The pharmaceutical formulations may comprise one or more carriers or excipients. Examples of carriers or excipients include any and all solvents, diluents, buffers (e.g., neutral buffered saline or phosphate buffered saline), solubilizers, colloids, dispersion media, vehicles, fillers, chelating agents (e.g., EDTA or glutathione), amino acids (e.g., glycine), proteins, disintegrants, binders, lubricants, wetting agents, emulsifiers, sweeteners, colorants, flavorings, aromatizers, thickeners, agents for achieving a depot effect, coatings, antifungal agents, preservatives, stabilizers, antioxidants, tonicity controlling agents, absorption delaying agents, and the like. Such materials may be non-toxic and should not interfere with the activity of the cells or active components. The precise nature of the carrier or excipient or other material may depend on the route of administration. For example, the pharmaceutical formulation may be in the form of a parenterally acceptable aqueous solution, which is pyrogen-free and has suitable pH, isotonicity and stability.

The pharmaceutical formulations may be in the form of, e.g., tablets, capsules, pills, powders, granulates, suspensions, emulsions, solutions, gels including hydrogels, pastes, ointments, creams, plasters, drenches, delivery devices, injectables, implants, sprays, or aerosols.

The pharmaceutical formulations may comprise one or more pharmaceutically acceptable salts. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Examples of pharmaceutically acceptable salts further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. It will be understood that, as used herein, references to specific agents (e.g., neuromedin U receptor agonists or antagonists), also include the pharmaceutically acceptable salts thereof.

In some embodiments, the pharmaceutical formulations may be a sustained-release formulation. Examples of sustained-release formulations include semipermeable matrices of solid hydrophobic polymers containing the proteins of the invention, which matrices are in the form of shaped articles, e.g., films, or microcapsule. Examples of sustained-release matrices include polyesters, hydrogels (for example, poly (2-hydroxyethyl-methacrylate), or poly(vinylalcohol)), polylactides, copolymers of L-glutamic acid and y ethyl-L-glutamate, non-degradable ethylene-vinyl acetate, degradable lactic acid-glycolic acid copolymers, and poly-D-(-)-3-hydroxybutyric acid.

When encapsulated proteins of the invention may remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

In some embodiments, the present disclosure further comprises a delivery device or system for administering the pharmaceutical formulations to a subject. Examples of the delivery devices or systems include encapsulation in liposomes, microparticles, microcapsules, minicells, polymers, capsules, tablets; and the like. In one embodiment, delivery device is a liposome. In a liposome, the active ingredient is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. In another embodiment, the pharmaceutical formulations can be delivered in a controlled release system including, but not limited to: a delivery pump (See, for example, Saudek, et al., New Engl. J. Med. 321: 574 (1989) and a semi-permeable polymeric material (See, for example, Howard, et al., J. Neurosurg. 71: 105 (1989)). Additionally, the controlled release system can be placed in proximity of the therapeutic target (e.g., a tumor or infected tissue), thus requiring only a fraction of the systemic dose. See, for example, Goodson, In: Medical Applications of Controlled Release, 1984. (CRC Press, Boca Raton, Fla.).

In some embodiments, the pharmaceutical formulations comprise an effective amount of the active ingredient(s) (e.g., a rhodanese, a functional fragment thereof, or a variant thereof, and/or or one or more modulating agents). The term "effective amount" refers to an amount which can elicit a biological or medicinal response in a tissue, system, animal or human that is being sought by a researcher, veterinarian, medical doctor or other clinician, and in particular can prevent or alleviate one or more of the local or systemic symptoms or features of a disease or condition being treated. In a particular embodiment, an effective amount of the active ingredient(s) may detoxify bacterial endotoxins and ameliorate a health problem caused or related to the bacterial endotoxins (e.g., their toxicity).

In some embodiments, the amount of the active ingredient(s) effective in the treatment of a particular disorder or condition depend on the nature of the disorder or condition, and may be determined by standard clinical techniques by those of skill within the art. In addition, in vitro assays may optionally be employed to help identify optimal dosage ranges. The precise dose to be employed in the formulation may also depend on the route of administration, and the overall seriousness of the disease or disorder, and may be decided according to the judgment of the practitioner and each patient's circumstances. In certain embodiments, the attending physician can administer low doses of the agent and observe the patient's response. Larger doses of the agent may be administered until the optimal therapeutic effect is obtained for the patient, and at that point the dosage is not increased further. In general, the daily dose range of a drug lie within the range known in the art for a particular drug or biologic. Effective doses may be extrapolated from dose-response curves derived from in vitro or animal model test systems. In some cases, appropriate duration of therapy using compositions of the present invention may be determined. Dosage will also vary according to the age, weight and response of the individual patient.

Deimmunization

The rhodanese in the pharmaceutical formulation may be deimmunized. The rhodanese may be deimmunized to render it non-immunogenic, or less immunogenic, to a given species (e.g., human). In some embodiments, the sequence of a rhodanese has been altered to eliminate one or more B- or T-cell epitopes. Deimmunization can be achieved through structural alterations to the polypeptide. Any deimmunization technique known to those skilled in the art can be employed. One suitable technique, for example, for deimmunizing proteins is described in WO 00/34317, the disclosure of which is incorporated herein in its entirety.

Enzyme Stabilization and Pharmacokinetic Techniques

Rhodaneses (e.g., those isolated from natural sources as well as engineered) may be used in both diagnostics and disease treatment. Alternative phosphatases (e.g., rhodanese with dephosphorylation activity) that have for example an altered (e.g., improved) specific activity, stability (e.g., in vivo $T_{1/2}$, or stability in respect of storage (e.g., shelf-life)) or substrate specificity. In some examples, the rhodanese may have increased thermal stability (e.g., by altering some of the amino acids sequences (e.g. introducing mutation corresponding to E102D of human rhodanese). Stabilization of the rhodanese may be achieved through structural alterations to the polypeptide. Any stabilization technique and strategies can be used to improve rhodanese stability, including thermal stability and plasma half-life time including but not limited to using Fc fusion or genetic fusion to albumin that can improve pharmacokinetic technique.

Additional Exemplary Formulations

In some embodiments, the composition may comprise a formulation alternative or in addition to a pharmaceutical formulation. Such alternative formulations may also comprise a rhodanese, a functional fragment thereof, or a variant thereof. Examples of such alternative formulations include food, food products, dairy products, and cells and microorganisms.

In some examples, provided herein include food or food products comprising a rhodanese, a functional fragment thereof, or a variant thereof. Examples of food or food products include meats, vegetables, plants, fruits, and flour-based products. In some cases, the food products comprise ingredients from an organism (e.g., animals or plants) that express or genetically modified to express rhodanese, a functional fragment thereof, or a variant thereof, and/or or one or more modulating agents. The food product may be from organisms (e.g., animals, plants, fungi, or microorganisms) that genetically modified to express the desired rhodanese, fragment thereof, or variants thereof. In some examples, the food product comprises an amount of rhodanese (TST) effective to modulate gastrointestinal tract flora levels in a subject. In some examples, the composition is a beverage product comprising an amount of rhodanese effective to modulate gastrointestinal tract flora levels in a subject.

In some examples, provided herein include dairy products, e.g., milk, butter, cheese, cream, and yogurt. In certain examples, the dairy products comprise non-pasteurized dairy or partially pasteurized milk or milk components. In a particular example, the dairy product comprises milk fat globule membrane component. In some cases, the dairy products may be from an animal (e.g., cow) that express or genetically modified to express rhodanese, a functional fragment thereof, or a variant thereof.

In some examples, provided herein include microorganisms. The microorganisms may produce (naturally or by genetic engineering), e.g., by secretion, a rhodanese, a functional fragment thereof, or a variant thereof. In some embodiments, the compositions comprise probiotics. In one example, the probiotics may be in enteric coated capsules or may be genetically modified probiotic capsules secreting/producing recombinant human/bovine liver rhodanese enzymes. In another example, the probiotics may be genetically modified probiotic producing recombinant human rhodanese and/or bovine liver rhodanese. In another example, the probiotics may be genetically modified probiotic secreting/producing both human and bovine rhodanese. In another example, the probiotics may be genetically modified probiotic secreting/producing human rhodanese or nutritional formulation.

Probiotics

In some embodiments, the microorganism are probiotics. By the term "probiotics" or "probiotic microorganisms" is meant non-pathogenic microorganisms that beneficially affect a subject by improving the intestinal microbial balance. Such probiotic microorganisms may preferably be anti-inflammatory microorganisms and/or from the group consisting of Lactic Acid Bacteria and *Bifidobacterium* spp. Lactic Acid Bacteria include all species, subspecies and strains of the following genera: *Carnobacterium, Enterococcus, Lactobacillus, Lactococcus, Leuconostoc, Oenococcus* and *Pediococcus*. Also covered are non-pathogenic species, subspecies and strains of the genus *Streptococcus* such as *Streptococcus salivarius* subsp. *thermophilus* or *Streptococcus thermophilus*.

The microorganisms may be of *Lactobacillus* spp., e.g., *Lactobacillus acetotolerans, Lactobacillus acidipiscis, Lactobacillus acidophilus, Lactobacillus agilis, Lactobacillus algidus, Lactobacillus alimentarius, Lactobacillus amylolyticus, Lactobacillus amylophilus, Lactobacillus amylovorus, Lactobacillus animalis, Lactobacillus arizonensis, Lactobacillus aviarius, Lactobacillus bifermentans, Lactobacillus brevis, Lactobacillus buchneri, Lactobacillus casei, Lactobacillus coelohominis, Lactobacillus collinoides, Lactobacillus coryniformis* subsp. *coryniformis, Lactobacillus coryniformis* subsp. *torquens, Lactobacillus crispatus, Lactobacillus curvatus, Lactobacillus cypricasei, Lactobacillus delbrueckii* subsp. *bulgaricus, Lactobacillus delbrueckii* subsp *delbrueckii, Lactobacillus delbrueckii* subsp. *lactis, Lactobacillus durianus, Lactobacillus equi, Lactobacillus farciminis, Lactobacillus ferintoshensis, Lactobacillus fermentum, Lactobacillus formicalis, Lactobacillus fructivorans, Lactobacillus frumenti, Lactobacillus fuchuensis, Lactobacillus gallinarum, Lactobacillus gasseri, Lactobacillus graminis, Lactobacillus hamsteri, Lactobacillus helveticus, Lactobacillus helveticus* subsp. *jugurti, Lactobacillus heterohiochii, Lactobacillus hilgardii, Lactobacillus homohiochii, Lactobacillus intestinalis, Lactobacillus japonicus, Lactobacillus jensenii, Lactobacillus johnsonii, Lactobacillus kefiri, Lactobacillus kimchii, Lactobacillus kunkeei, Lactobacillus leichmannii, Lactobacillus letivazi, Lactobacillus lindneri, Lactobacillus malefermentans, Lactobacillus mali, Lactobacillus maltaromicus, Lactobacillus manihotivorans, Lactobacillus mindensis, Lactobacillus mucosae, Lactobacillus murinus, Lactobacillus nagelii, Lactobacillus oris, Lactobacillus panis, Lactobacillus pantheri, Lactobacillus parabuchneri, Lactobacillus paracasei* subsp. *paracasei, Lactobacillus paracasei* subsp. *pseudoplantarum, Lactobacillus paracasei* subsp. *tolerans, Lactobacillus parakefiri, Lactobacillus paralimentarius, Lactobacillus paraplantarum, Lactobacillus pentosus, Lactobacillus perolens, Lactobacillus plantarum, Lactobacillus pontis, Lactobacillus psittaci, Lactobacillus reuteri, Lactobacillus rhamnosus, Lactobacillus ruminis, Lactobacillus sakei, Lactobacillus salivarius, Lactobacillus salivarius* subsp. *salicinius, Lactobacillus salivarius* subsp. *salivarius, Lactobacillus sanfranciscensis, Lactobacillus sharpeae, Lactobacillus suebicus, Lactobacillus thermophilus, Lactobacillus thermotolerans, Lactobacillus vaccinostercus, Lactobacillus vaginalis, Lactobacillus versmoldensis, Lactobacillus vitulinus, Lactobacillus vermiforme, Lactobacillus zeae*. In one example, the microorganism is *Lactobacillus plantarum*.

The microorganisms may be of *Bifidobacterium* spp., e.g., *Bifidobacterium adolescentis, Bifidobacterium aerophilum, Bifidobacterium angulatum, Bifidobacterium animalis, Bifidobacterium asteroides, Bifidobacterium bifidum, Bifidobacterium bourn, Bifidobacterium breve, Bifidobacterium catenulatum, Bifidobacterium choerinum, Bifidobacterium coryneforme, Bifidobacterium cuniculi, Bifidobacterium dentium, Bifidobacterium gallicum, Bifidobacterium gallinarum, Bifidobacterium indicum, Bifidobacterium longum, Bifidobacterium longum* bv *longum, Bifidobacterium longum* bv. *infantis, Bifidobacterium longum* bv. *suis, Bifidobacterium magnum, Bifidobacterium merycicum, Bifidobacterium minimum, Bifidobacterium pseudocatenulatum, Bifidobacterium pseudolongum, Bifidobacterium pseudolongum* subsp. *globosum, Bifidobacterium pseudolongum* subsp. *pseudolongum, Bifidobacterium psychroaerophilum, Bifidobacterium pullorum, Bifidobacterium ruminantium, Bifidobacterium saeculare, Bifidobacterium scardovii, Bifidobacterium subtile, Bifidobacterium thermoacidophilum, Bifidobacterium thermoacidophilum* subsp. *suis, Bifidobacterium thermophilum, Bifidobacterium urinalis*.

In some examples, examples of the probiotics include *Saccharomyces boulardii*; *Lactobacillus rhamnosus* GG; *Lactobacillus plantarum* 299v; *Clostridium butyricum* M588; *Clostridium difficile* VP20621 (non-toxigenic *C. difficile* strain); combination of *Lactobacillus casei, Lactobacillus acidophilus*; combination of *Lactobacillus casei, Lactobacillus bulgaricus, Streptococcus thermophilus*; combination of *Lactobacillus acidophilus, Bifidobacterium bifidum*; combination of *Lactobacillus acidophilus, Lactobacillus bulgaricus delbrueckii* subsp. *bulgaricus, Lactobacillus bulgaricus casei, Lactobacillus bulgaricus plantarum, Bifidobacterium longum, Bifidobacterium infantis, Bifidobacterium breve, Streptococcus salivarius* subsp. *thermophilus*.

Methods of Treatment

In another aspect, the present disclosure provides methods for treating a health condition resulted from or related to a bacterial endotoxin. For example, the health condition may be resulted from or related to the toxicity of the bacterial endotoxin.

In general, the methods comprise administering a composition or a pharmaceutical formulation descried herein, e.g., a composition or pharmaceutical formulation comprising a rhodanese or a functional domain thereof, where the rhodanese is capable of detoxifying the bacterial endotoxin, to a subject in need thereof.

In some examples, the methods comprise administering the composition orally. In some examples, the method comprise administering the composition topically. In some cases, the administration is to deliver the composition to the mucosal layer of the gastrointestinal tract, and or complex, e.g., the upper gastrointestinal tract mucosa rhodanese. In a particular example, the composition is administered to the mucosal tissues of the gastrointestinal tract of a mammal for in situ detoxification of the mucosal layer of the gastrointestinal tract, and or complex. In some examples, the methods comprise administering the composition via IV infusion. The administration may be performed parenterally, rectally, orally or topically, intravenously, intramuscularly, subcutaneously, peritoneally, peridurally, nasal, pulmonarily, or mucosally.

In some embodiments, the methods include administering the composition at or at about the same time as (e.g., concurrent with) a surgical procedure, or at about the same time as, or as soon as possible after, the subject suffers a traumatic injury, e.g., within 2, 4, 6, 8, 10, 12, 24, 48, or 96 hours.

In some embodiments, the methods also include administering an antibiotic, e.g., before, at the same time, or after the composition is administered. In such methods, the amount of rhodanese can be, for example, from about 1 to about 10,000 units, e.g., 1 to 200, 200 to 500, 500 to 1,000, 1,000 to 5,000, or 5,000 to 10,000 units. Higher doses, e.g., 10,000 to 50,000 units, are also possible. These dosages can be administered over one or more hours or days. As used herein, one unit refers to the amount of an enzyme that catalyzes the conversion of one micromole of substrate per minute under specified conditions of the assay method. For example, a unit of rhodanese as used herein may refer to the amount of rhodanese that catalyzes the dephosphorylation of one micromole of substrate per minute under the conditions of the assay described in Examples 1 and 2.

The endotoxins may be from Gram-positive bacteria. The endotoxins may be from *Clostridium* (e.g., *Clostridium difficile*), *Escherichia* (e.g., *Escherichia coli*), *Bordetella*, *Blanchamera*, *Salmonella*, *Haemophilus*, *Klebsiella*, *Proteus*, *Enterobacter*, *Pseudomonas*, *Pasteurella*, *Acinetobacter*, *Chlamydia*, and *Neisseria*. In one example, the endotoxin is LPS. In another example, the endotoxin is from *Clostridium difficile* (*C. diff*). In another example, the endotoxin is from *E coli*. In a particular example, the endotoxin is LPS from *C. diff*. In another example, the endotoxin is LPS from *E coli*. Examples of endotoxins include lipopolysaccharide (LPS), lipid A, Lipoteichoic acid (LTA), and lipooligosaccharide (LOS).

The methods can include administering the composition by irrigation of the affected area. The methods can also include administering the composition topically to the affected area.

Examples of health conditions include bacterial infection (e.g., infection by Gram-negative bacteria), bowel diseases, *Clostridium difficile* infection, modulation of gut microbiota, antibiotic-associated diarrhea (AAD), gastrointestinal tract infections, abdominal infections, alternation of bacterial over growth, Small intestinal bacterial overgrowth, sepsis, septic shock, systemic inflammatory response syndrome, meningococcemia, trauma, hemorrhagic shock, burns, surgery, organ transplantation, liver diseases, pancreatitis, enterocolitis, periodontal diseases, pneumonia, cystic fibrosis, asthma, coronary heart diseases, congestive heart failure, kidney diseases, hemolytic uremic syndrome, renal dialysis, preserving renal function, autoimmune diseases, cancers, Alzheimer's disease, rheumatoid arthritis, lupus, systemic lupus erythematosus, metabolic disorders, obesity, diabetes, dyslipidemia, insulin resistant syndromes, metabolic syndrome, steatohepatitis, fatty liver, non-alcoholic fatty liver diseases, hyperglycemia, glucose intolerance, impaired glucose tolerance, insulin resistance, hyperlipidemia, hypertriglyceridemia, hypercholesterolemia, low HDL levels, high LDL levels, abdominal obesity, atherosclerosis, hypertension, and cardiovascular diseases. In one example, the health condition may be host-defense resistance.

In some examples, the health conditions may be LPS-mediated, LPS-induced, or LPS-exacerbated diseases. In some cases, the health conditions may be disorders including kidney, liver, gastrointestinal tract, abdominal infections, and lungs injuries generated by Gram-positive bacterial infection/LPS.

In some examples, the method may be used for modulating gastrointestinal tract flora levels in a subject, the method comprising administering to the subject a composition with an amount of rhodanese or variant thereof effective to increase the number of commensal bacteria in the gastrointestinal tract, decrease the number of pathogenic bacteria in the gastrointestinal tract, or increase the number of commensal bacteria and decrease the number of pathogenic bacteria in the gastrointestinal tract, thereby modulating gastrointestinal tract flora levels in the subject.

Additional Exemplary Applications

In another aspect, the present disclosure provides methods for making reagents, vaccines, and pharmaceutical formulations. In some embodiments, reagents, vaccines, and pharmaceutical formulations may comprise bacterial endotoxins when originally made. The methods may comprise incubating the compositions with the reagents, vaccines, and pharmaceutical formulations, wherein the composition detoxifies the bacterial endotoxins.

In certain examples, it may be desirable to have bacterial endotoxins in reagents, vaccines, or pharmaceutical formulations, but such applications may be limited by the toxicity of the endotoxins. In such cases, the compositions herein may be used to detoxify the endotoxins. The detoxified endotoxins may then be used in reagents, vaccines, or pharmaceutical formulations, e.g., as adjuvants in vaccines or vaccine antigens.

Protein Production

The rhodanese, fragments thereof, and variants thereof may be produced by recombinant techniques well known in the art. See, e.g., Green and Sambrook, Molecular Cloning: A Laboratory Manual, 4th edition (2012). These engineered polypeptides produced by recombinant technologies may be expressed from a polynucleotide. One skilled in the art will appreciate that the polynucleotides, including DNA and RNA, that encode such engineered polypeptides may be obtained from the cDNA of rhodanese, fragments thereof, or variants thereof, taking into consideration the degeneracy of codon usage, and may further engineered as desired to incorporate the indicated substitutions. These polynucleotide sequences may incorporate codons facilitating transcription and translation of mRNA in microbial hosts.

Host cells may be transformed with the expression or cloning vectors for protein production and cultured in conventional nutrient media modified as appropriate for inducing promoters, selecting transformants, or amplifying the genes encoding the desired sequences. The host cells used to produce the proteins of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. The media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In some cases, the protein may be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

In some cases, the protein may be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis.

The proteins of may be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, more preferably at least 95% pure, and most preferably at least 98% pure. Regardless of the exact numerical value of the purity, the polypeptide is sufficiently pure for use as a pharmaceutical product.

EXAMPLES

Example 1—Detoxification of Bacteria Endotoxin (LPS) in Zebrafish

This example demonstrates that endogenous rhodanese detoxified LPS encountered by the intestinal epithelium, liver, kidneys and lungs where rhodanese expression high. First, Applicant tested whether dephosphorylated LPS was less toxic to zebrafish by exposing 7 dpf zebrafish larvae to 150 µg/ml LPS that had been pre-incubated with bovine liver rhodanese (TST). Preincubated LPS was completely non-toxic to zebrafish, whereas mock treated LPS at the same dose caused 100% lethality by 5 hours. To generate detoxification LPS, LPS was incubated with 10 U/ml rhodanese from bovine liver for 5 h at 37° C., then incubated at 80° C. for 10 min to destroy rhodanese enzyme activity. Mock treated LPS was generated by incubating LPS under same conditions without the addition of bovine rhodanese enzyme.

Example 2—Detoxification of Bacteria Endotoxin (LPS) by Engineered Rhodanese Applicant generated engineered rhodanese by introducing mutations to human rhodanese. FIG. 2 shows site-directed mutagenesis of recombinant human rhodanese enzyme dephosphorylates the E. coli's LPS.

By site-directed mutagenesis (SDM) as shown in FIG. 2, engineered human rhodanese had ability to rapidly dephosphorylates the E. coli' LPS as it is shown in FIG. 3. The site-directed mutagenesis human rhodanese enzyme had the active-site loop, which was formed by seven residues instead of the six as in the wildtype human rhodanese. This resulted in a wider catalytic pocket that accommodated a phosphorous atom, which had a van der Waals radius slightly larger than a sulfur atom. To test the detoxification function of the engineered human rhodanese (shown as "recTST" in FIG. 3), LPS was pre-incubated with the engineered human rhodanese (5-100 units/ml) for 37° C. for 30 min at 1 µg/ml LPS. In contrast, for negative controls heat-inactivated (95° C. for 1 h) engineered human rhodanese were added to the reaction mixture with 1 µg/ml LPS. To detect inorganic phosphorus (Pi) released from the LPS, malachite green solution (25 µl) was added for 10 min, and activity was then determined from spectrophotometric absorbance readings (650 nm wavelength) taking into account the background readings as it was described in (Chen K T et al., Am J Physiol Gastrointest Liver Physiol. 2010 August; 299 (2):G467-75). Each assay was performed in triplicate.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A composition comprising an engineered or non-naturally occurring rhodanese comprising a phosphate-binding motif, wherein the phosphate-binding motif comprises a sequence of $CX_1X_2X_3X_4X_5R$, wherein each of $X_1$-$X_5$ represents a single amino acid.

2. The composition of claim of claim 1, wherein
$X_1$ is E or R;
$X_2$ is Y, F, E, T, K, or G;
$X_3$ is S or G;
$X_4$ is S or G; and
$X_5$ is V or E.

3. The composition of claim 2, wherein the phosphate-binding motif comprises a sequence of SEQ ID NOs: 3-15.

4. The composition of claim 3, wherein the phosphate-binding motif comprises a sequence of SEQ ID NO: 3.

5. The composition of claim 1, wherein the rhodanese comprises a sequence of SEQ ID NO: 16.

6. The composition of claim 1, wherein the rhodanese has a dephosphorylation activity.

7. The composition of claim 1, wherein the rhodanese is capable of dephosphorylating a bacterial endotoxin.

8. The composition of claim 7, wherein the bacterial endotoxin is lipopolysaccharide (LPS) or lipoteichoic acid (LTA).

9. The composition of claim 1, wherein the rhodanese is or is derived from a mammalian intestine rhodanese, human rhodanese, or bovine liver rhodanese or synthetic polypeptides contain modified rhodanese domains.

10. The composition of claim 1, wherein the phosphate-binding motif is comprised in a modified active-site loop of a rhodanese.

11. The composition of claim 10, wherein the active site loop is modified at one or more amino acids corresponding to amino acids 248-253 of SEQ ID NO: 1.

12. The composition of claim 10, wherein the modified active-site loop comprises one or more insertions, deletions, or substitutions of amino acid residues in the active-site loop relative to a wild-type rhodanese.

13. The composition of claim 10, wherein the modification comprises 1, 2 or 3 amino acid insertions in the active-site loop.

14. A pharmaceutical formulation comprising the composition of claim 1.

15. The pharmaceutical formulation of claim 14, further comprising a stabilizer, activator, carrier, osmotic agent, propellant, disinfectant, protective agent, diluent, nutritional agent, excipient, or a combination thereof.

16. The pharmaceutical formulation of claim 14, wherein the pharmaceutical formulation is a vaccine.

17. A method for treating a health condition induced by a bacterial endotoxin, the method comprising administering a composition comprising an effective amount of the composition of claim 1.

18. The method of claim 17, wherein the administration is performed orally, topically, or intravenously.

19. The method of claim 17, wherein the health condition is a LPS-mediated, LPS-induced, or LPS-exacerbated disease.

20. The method of claim 17, wherein the health condition is bowel diseases, *Clostridium difficile* infection, modulation of gut microbiota, alternation of bacterial over growth, Small intestinal bacterial overgrowth, antibiotic-associated diarrhea (AAD), gastrointestinal tract infections, abdominal infections, sepsis, septic shock, systemic inflammatory response syndrome, meningococcemia, trauma, hemorrhagic shock, burns, surgery, organ transplantation, liver diseases, pancreatitis, enterocolitis, periodontal diseases, pneumonia, cystic fibrosis, asthma, coronary heart diseases, congestive heart failure, kidney diseases, hypophosphatasia, hemolytic uremic syndrome, renal dialysis, preserving renal function, autoimmune diseases, cancers, Alzheimer's disease, rheumatoid arthritis, lupus, systemic lupus erythematosus, metabolic disorders, obesity, diabetes, dyslipidemia, insulin resistant syndromes, metabolic syndrome, steatohepatitis, fatty liver, non-alcoholic fatty liver diseases, hyperglycemia, glucose intolerance, impaired glucose tolerance, insulin resistance, hyperlipidemia, hypertriglyceridemia, hypercholesterolemia, low HDL levels, high LDL levels, abdominal obesity, atherosclerosis, hypertension, and cardiovascular diseases, or a combination thereof.

21. The method of claim 17, wherein the health condition is an infection by one or more bacteria producing the endotoxin.

22. The method of claim 17, wherein the composition is effective to increase the number of commensal bacteria in the gastrointestinal tract, decrease the number of pathogenic bacteria in the gastrointestinal tract, or increase the number of commensal bacteria and decrease the number of pathogenic bacteria in the gastrointestinal tract, thereby modulating gastrointestinal tract flora levels in the subject.

23. A method of making a pharmaceutical formulation comprising a non-toxic bacterial endotoxin, the method comprising detoxifying a toxic endotoxin with the composition of claim 1, thereby producing the non-toxic bacterial endotoxin.

* * * * *